United States Patent [19]

Chastain et al.

[11] Patent Number: 5,994,598
[45] Date of Patent: Nov. 30, 1999

[54] METHOD OF PREPARING PERILLYL ALCOHOL AND PERILLYL ACETATE

[75] Inventors: Doyle E. Chastain, 137 Birch St., Titusville, Fla. 32780; Naresh Mody, Merritt Island, Fla.; George Majetich, Athens, Ga.

[73] Assignee: Doyle E. Chastain, Titusville, Fla.

[21] Appl. No.: 09/007,345

[22] Filed: Jan. 15, 1998

[51] Int. Cl.[6] ........................................ C07C 29/09

[52] U.S. Cl. ............................... 568/827; 560/249

[58] Field of Search ................................ 568/827; 560/249

[56] References Cited

U.S. PATENT DOCUMENTS

| 3,956,404 | 5/1976 | Walling et al. | 260/635 |
| 5,110,832 | 5/1992 | Chastain et al. | 514/729 |
| 5,370,877 | 12/1994 | Gould et al. | 514/529 |

*Primary Examiner*—James H. Reamer
*Attorney, Agent, or Firm*—Arthur G. Yeager

[57] ABSTRACT

A process for preparing perillyl alcohol by converting beta-pinene oxide into an alcohol in an acidic reaction medium, esterifying said alcohol to produce a mixture containing perillyl acetate, and hydrolyzing said perillyl acetate to perillyl alcohol.

11 Claims, 1 Drawing Sheet

METHOD OF PREPARING PERILLYL ALCOHOL AND PERILLYL ACETATE

CROSS-REFERENCE TO RELATED APPLICATIONS

Not Applicable

STATEMENT REGARDING FEDERALLY SPONSORED RESEARCH OR DEVELOPMENT

Not Applicable

REFERENCE TO A MICROFICHE APPENDIX

Not Applicable

BACKGROUND OF THE INVENTION (1) Field of the Invention

This invention relates to a method of preparing perillyl alcohol and perillyl acetate from beta-pinene oxide. The chemical structures of these compounds are shown below.

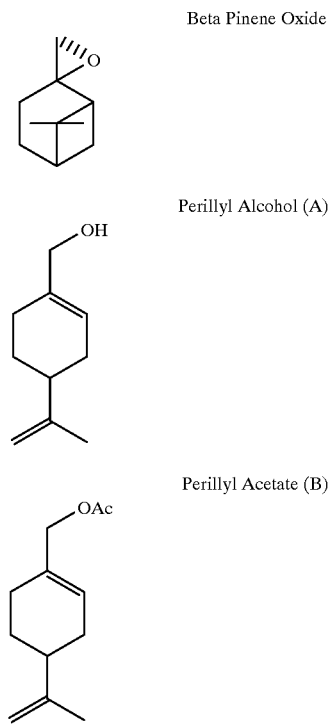

Beta Pinene Oxide

Perillyl Alcohol (A)

Perillyl Acetate (B)

(2) Description of the Related Art

In U.S. Pat. No. 5,110,832 Chastain and Sanders showed the monoterpene perillyl alcohol has a wide spectrum of antimicrobial activity against virtually all bacteria and yeast. Because it is readily biodegradable, and considered environmentally safe, it has numerous potential uses as a bactericide and an anti-yeast compound in agricultural, industrial, pharmaceutical, and consumer products. Perillyl alcohol inhibits dental plaque and is likely to be used in mouthwash, toothpaste, and chewing gum. Uses in topical pharmaceutical and veterinary products to control normal and resistent pathogens have been suggested. Perillyl alcohol (A) is an excellent general antiseptic. In laboratory animals perillyl alcohol is non-toxic in bactericidal concentrations and is likely to find utility as a preservative for food, medicine, and cosmetics, and as an antiseptic for food processing equipment. Perillyl alcohol can be used as a bactericide in industrial cutting oils, air filters, and as a spray for bacterial and yeast diseases that infect plants.

In tissue cultures perillyl alcohol was found to have excellent antineoplastic activity against carcinomas of the breast, pancreas, lung, and colon. Antineoplastic concentrations of perillyl alcohol, when administered orally, were demonstrated to be non-toxic in dogs and rats. Gould et all found perillyl acetate to exhibit significant antineoplastic activity in treating and preventing carcinoma of the breast in rats. D. McNamee's pharmacokinetics studies suggested that perillyl alcohol may be a procompound that acts via its metabolites.

Recent efforts of the Environmental Protection Agency to rid the environment of formaldehyde makes perillyl alcohol an ideal candidate as a general disinfectant and as an embalming fluid. When added to hydrocortisone cream, perillyl alcohol will likely find efficacy as a topical bactericide, anti-yeast and antipruritic cream.

Perillyl alcohol, the main ingredient of lavender oil, is obtained from a hybrid of true lavender and spike lavender plants. It has enjoyed a prominent position in both the cosmetic and the perfume industry because it blends well with other essential oils, improves the texture of cosmetics and has virtually no odor. Synthetic perillyl alcohol has been costly and used only in the most expensive perfumes.

In the future, large quantities of perillyl alcohol will be needed for use as microbicides, as antineoplastic agents, as preservatives, and for use in perfumes and fragrances.

Blumann in Chemical Abstracts, Volume 63 1965 on page 1819, produced perillyl alcohol by the oxidation of limonene, and Bardychev substantiated that perillyl alcohol can be produced by the oxidation of limonene as outlined in Chemical Abstracts, Volume 80, 1974, page 359. In German Offen 2,513,910 and Canadian Patent No. 1,077,959 H. R. Ansari and P. Fido produced perillyl alcohol by the acetylation of limonene.

Perillyl alcohol can be produced by reacting limonene with selenium dioxide (that is toxic) and other oxidants (that are difficult to work with i.e., anhydrous chromium trioxide) to yield various oxidation products, including a small amount of perillaldehyde. Once isolated, perillaldehyde is reduced to afford perillyl alcohol. While this two-step process is conceptually attractive, the oxidation of limonene to give perillyl alcohol proceeds in a low overall yield.

Several routes have been have been developed to produce perillyl alcohol from beta pinene. For example, Walling made perillyl alcohol (Canadian Patent No. 981,695) by reacting benzyl peroxide with beta pinene followed by alkaline hydrolysis to perillyl alcohol. In 1967 a process for preparing perillyl alcohol was described in British Patent 1,094,875 (Nippon Terpene) wherein beta pinene was oxidized by lead tetracetate in the presence of fatty acid dissolved in glacial acetic acid that was subsequently hydrolyzed to perillyl alcohol with a yield of only forty-five (45%) percent. Similarly, beta pinene was oxidized with $Pb_3O_4$ in glacial acetic acid to form perillyl alcohol (Barton et al. J. Clem. Soc. Perkin Trans. I 614 1972). In 1972 in German Offen 2,162,882, M. Julia made perillyl alcohol by oxidizing beta pinene with a benzoxyloxy radical, generated by ammonium persulfate oxidation of a benzoate anion.

Among other routes that have been developed to prepare perillyl alcohol from beta pinene oxide is that reported by T. K. Keenan in 1966 who produced perillyl acetate from beta-pinene oxide by refluxing beta-pinene oxide with acetic anhydride and acetic acid for seven hours followed by removal of the acetate to afford a nine percent (9%) yield of perillyl alcohol based on the starting beta-pinene oxide (B.S. Thesis Mass. Institute of Tech.). The applicants found the process to be reproducible albeit in low yield. F. C. Delay in Swiss Patent 5671/84 reported the production of perillyl alcohol in which he treated beta-pinene oxide with nitromethane and ammonium nitrite at a temperature between 20° C. and 90° C. in an overall yield of thirty percent (30%). Two years later Wang and co-workers published in Tetrahedron 1986, 620–638 complete details of this procedure and reported an overall yield of sixty-eight percent (68%) perillyl alcohol.

In 1980 Lazare and co-workers reported a ninety percent (90%) yield of a diol that was obtained by treating beta-pinene oxide with mercury (II) salts in tetrahydrofuran/water solutions. (J. Chem. Soc. Perkin Trans I 1980, 1747). The diol was extracted with chloroform followed by its reaction with 1.5 N. hydrochloric acid to give an eighty-five percent (85%) yield of perillyl alcohol based on the initial beta pinene oxide. The applicants could not reproduce the acid-catalyzed dehydration using 1.5 N HCl despite trying numerous variations of the experimental conditions reported. The applicants found this process to produce perillyl alcohol in a yield of less than ten percent. In every case complex mixtures of products were obtained. It was stated that both p-menth-1-ene-7, 8 diol and 7-acetoxy-p-menth-1-en-8-ol are fragrance compounds but no experimental procedures describing their preparation were presented.

In 1986 Ohloff and Giersch (Helv. Chim. Acta 1980 63, 83) prepared p-menth-1-ene-7, 8-diol in high yield by stirring beta-pinene oxide in water and then continuously adding solid carbon dioxide to the mixture. This reaction is pH dependent, requires very careful monitoring to prevent serious workup problems, and is considered a poor commercial process. The p-menth-1-ene-7, 8-diol produced in this fashion was used for purposes other than preparing perillyl alcohol.

BRIEF SUMMARY OF THE INVENTION

The applicants have developed two preferred methods of preparing perillyl alcohol and/or its acetate from beta pinene oxide that are simple and efficient processes. These processes have been carried out on batches of up two hundred grams and are commercially viable processes that have a major advantage of utilizing common, environmentally safe reagents.

The following examples are illustrative of the best mode for carrying out the invention. They are, obviously, not to be construed as limitative of the invention since various other embodiments can readily be evolved in view of the teachings provided herein. In example 1, the method used by Hill et al[6] to convert beta pinene to beta pinene oxide is outlined. In examples 2–4 and 5–8 the applicants detail their first and second preferred methods of producing perillyl alcohol and/or its acetate from beta pinene oxide. In Example 9 formulations of perillyl alcohol that kill bacteria and yeast are presented.

The applicant's first preferred method of preparing perillyl alcohol from pure beta pinene oxide is to react pure beta pinene oxide with anhydrous sodium acetate and glacial acetic acid to produce p-menth-1-en-8-acetoxy-7-ol (C), after which the p-menth-1-en-8-acetoxy-7-ol is pyrolyzed to perillyl alcohol in a yield of approximately fifty percent (50%). This represents a facile two step procedure using inexpensive, safe reagents. The applicant's second preferred method of producing perillyl acetate and perillyl alcohol from pure beta pinene oxide is to react pure beta pinene oxide with an acid resin to produce p-menthene-7,8-diol (D) that is then acetylated to afford 7-acetoxy-p-menth-1-en-8-ol (E) which is then dehydrated by any of five different procedures to yield perillyl acetate that can be hydrolyzed to perillyl alcohol.

The two methods are delineated below.

Method (1):

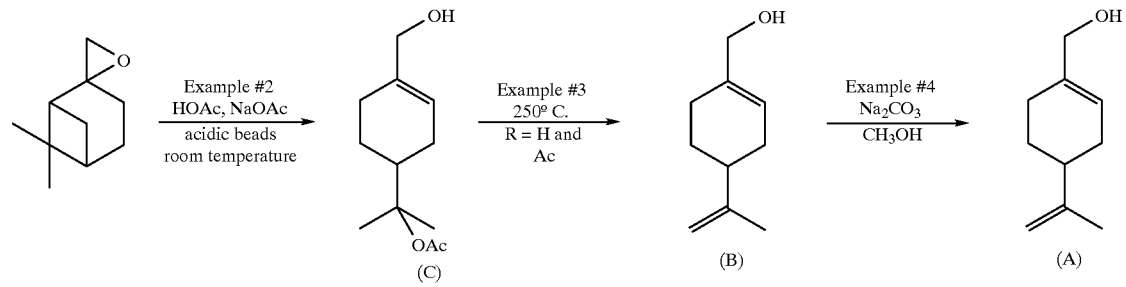

Method (2):

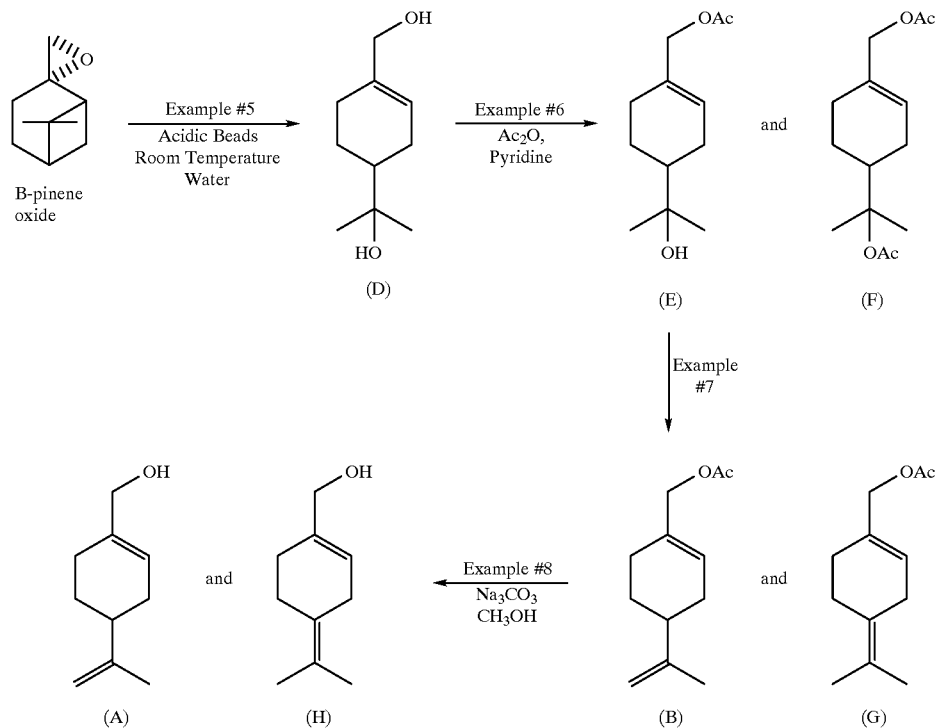

DETAILED DESCRIPTION OF THE INVENTION

Figure 1:
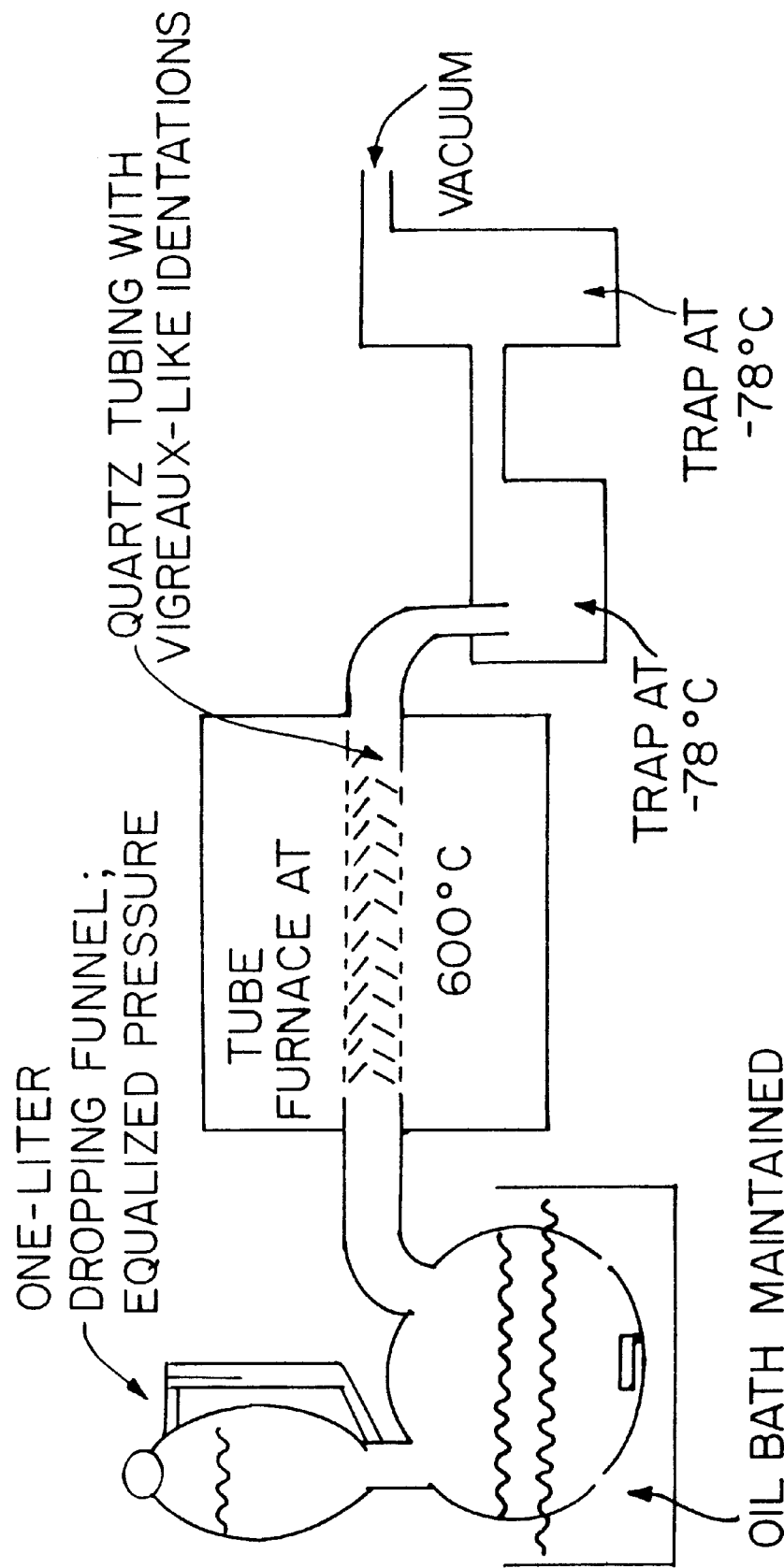
FIG. 1 is a diagrammatic view depicting the reaction set-up used to carry out flash vacuum pyrolysis in the process of this invention.

The following description represents the various embodiments of the invention, including working examples where applicable.

EXAMPLE ONE

Preparation of beta pinene oxide

The conversion of beta pinene to beta pinene oxide is the first step in preparing perillyl alcohol or perillyl acetate. The method outlined by Hill to convert beta pinene to beta pinene oxide follows.

To a mixture of one kilogram (7.35 moles) of beta pinene and 2.5 kilos of powdered anhydrous sodium carbonate in five liters of dry methylene chloride that was constantly stirred in an ice bath, was added dropwise, 1550 ml (8.08 moles or 1.1 equivalents) of forty percent (40%) peracetic acid containing 20 grams of sodium acetate. The mixture was stirred at room temperature until the solution gave a negative starch-iodine test. The solid salts were removed by suction filtration and washed well with additional methylene chloride. The solvent was removed using a rotary evaporator and the residue was distilled under vacuum (bp 64–66° C. at 4.2 mm Hg) to yield 870 grams (85%) beta pinene-oxide.

Alternatively, beta pinene oxide was isolated from Rosemarel. Beta pinene and other terpenoid contaminants were separated from the Rosemarel by means of distillation using a five foot, silver-jacketed vigreaux column. Distillate was collected from 0–65° C. at water aspirator pressure. NMR analysis indicated that the resulting distillation residue consisted predominantly of beta pinene oxide and required no further purification.

The applicants first preferred method of preparing perillyl alcohol follows in examples two through four.

EXAMPLE TWO

The preparation of p-menth-1-en-8-acetoxy-7-ol (C)

To a twelve liter three-neck round bottom flask equipped with a mechanical stirrer was added one kilo of fused anhydrous sodium acetate, (dried under 1 mm Hg vacuum for a 12 hour period), 50 grams of Amberlite IRC-50 Beads and 6 liters of glacial acetic acid. The mixture was stirred while it was cooled to room temperature. To this mixture was added one kilo of beta pinene oxide over a five minute period through an addition funnel after which the temperature increased rapidly to 65 ° C. The stirring was continued for two hours after which the mixture had returned to room temperature. One liter of glacial acetic acid was added to the reaction mixture and the resulting mixture was filtered through a course-sintered glass funnel. The solids were washed with glacial acetic acid (500 ml). The acetic acid was removed from the combined organic phases by distillation (14 hours; 4.5 liters of acetic acid recovered). After the residue was cooled to room temperature, two liters of tert-butyl methyl ether was added. The solids were removed by suction filtration and washed again with one liter of tert-butyl methyl ether. The ethereate solutions were combined and the solvent was removed by water aspirator to provide 1051 grams of crude residue that consisted of acetate B, perillyl alcohol, acetate C and byproducts. It is important to note that when Amberlite and glacial acetic acid were added to the anhydrous sodium acetate, the mixture had to be cooled to room temperature before the addition of epoxide to prevent the formation of undesired aldehydes and the mixture had to be stirred for several minutes to allow saturation of the acetic acid with the sodium acetate. The optimum quantity of sodium acetate needed to suppress the formation of undesired aldehydes was not determined. Failure to use dry sodium acetate greatly simplifies the workup procedure but results the formation of up to 20% of the aldehyde by-product that is easily removed by fractional distillation. Although this reaction was exothermic, it did not become a run away. After beta pinene oxide is added, failure to remove as much acetic acid as possible, results in the formation of an emulsion when organic solvents such as ether, hexane, toluene or THF are added. On a bench scale it is not important for the reaction to be stirred, but on an industrial scale the presence of sodium acetate (that is needed to inhibit side reactions) becomes troublesome and can be removed from the reaction mixture by the addition of a filtering aid such as Celite. The following NMR data were obtained on a sample of p-menth-1-en-8-acetoxy-7-ol (C):

$^1$H NMR of menth-1-en-8-acetoxy-7-ol (C): (250 MHz)) δ 1.20–1.50 (m, 8H), 1.41 (s, 3H), 1.45 (s, s, 3H), 1.75–2.20 (m, 9H), 1.95 (s, 3H), 3.98 (br.s, 2H), 5.653 (br.s, 1H).

$^{13}$C NMR of menth-1-en-8-acetoxy-7-ol (C): (250 MHz) 170.5 (s), 137.4 (s), 121.9 (d), 84.6 (s), 66.8 (t), 42.6 (q), 26.3 (t), 26.0 (t), 23.2 (t), 23.4 (q), 23.1 (d) ppm.

EXAMPLE THREE

The Pyrolysis of (C), followed by Acetylation, to Provide Perillyl Acetate

In the preparation of olefins, flash vacuum thermolysis (FTV) eliminates acetates, tosylates, or xanthines at lower temperatures than those required for the dehydration of alcohols[9]. We have found that the loss of acetic acid from the acetate (C) can be easily achieved thermally without the need to use expensive pyrolysis devices.

1051 grams of the crude acetate (C) were added to a two liter three-necked flask equipped with an overhead mechanical stirrer, a thermometer capable of monitoring temperatures less than 300° C., and a distillation head with a condenser and Claisen adapter. To the reaction vessel was added one kilo of anhydrous sodium carbonate powder. The resulting slurry was allowed to sit at room temperature for one hour to allow trace acetic acid to be neutralized by the $Na_2CO_3$. A vacuum distillation apparatus was attached to the flask after which the whole system was subjected to 1.0 mm Hg vacuum, followed by nitrogen flushing to place the reaction vessel under an inert atmosphere at atmospheric pressure. The reaction mixture was then slowly heated using either a Woods metal bath or a Glas-col heater using dry sea sand to fill any empty space between the heating unit and the reaction vessel. Once an external temperature greater than 200° C. was reached, the distillation of low boiling volatiles (<90° C.) and water was observed. At this stage the internal temperature of the reaction mixture was ~120° C. External heating was maintained at temperatures between 250° C. and 280° C. while the internal temperature of the stirred reaction mixture ultimately reached a temperature of 250° C. Although the pyrolysis was complete at this stage heating was continued for an additional 30 minutes at an internal temperature of 250° C. The reaction vessel was removed from the heat source and allowed to cool to room temperature after which one liter of tert-butyl methyl ether was added to the flask. The salts were filtered off by suction filtration and washed with another 500 ml of fresh tert-butyl methyl ether. The filtrates were combined and the solvent was removed under vacuum to afford 897 grams of a mixture of acetate B, perillyl alcohol, and by-products in the crude ratio of 15:5:1.

The thermolysis of acetate (C) must be carried out under an inert atmosphere to prevent the auto-oxidation of perillyl alcohol to perillyl aldehyde. The temperature during the thermolysis is critical. The applicants found the temperature of 250° C. to be ideal. If the pyrolysis temperature is too high, more elimination and aromatization side products such as cumenes form. Following the thermolysis it is important to filter off all salts with tert-butyl methyl ether because they are difficult to eliminate in the next stage, and if not removed adversely effect the distillation. On several occasions the reaction mixture was diluted with water and any remaining undissolved sodium carbonate used was carefully solubilized with 5% aqueous HCl and then the combined aqueous phases were extracted with tert butyl methyl ether. Reactions run on less than a 200 gram scale did not require stirring and could employ pre-heated bathes, but reactions run on one kilo batches required stirring to insure complete conversion. While either a Woods bath or a simple Glas-col heater could be used, it is crucial that the temperature of the external reaction mixture to be greater than 250° C., otherwise the pyrolysis is painfully slow.

It is recognized by the applicants that a modification of the pyrolysis equipment, for example a hot column apparatus or a heated autoclave, and the conditions of the pyrolysis can increase or decrease the yield of perillyl alcohol.

Perillyl alcohol can be separated from the perillyl acetate at this stage via fractional distillation using an efficient five foot vigreaux column provided the distillation was carried out at less than one torr. However, it was found to be more practical to acetylate the crude mixture to only perillyl acetate (B) rather than to carry out a careful distillation. Extensive study established that perillyl acetate was far less prone to polymerize during distillation than perillyl alcohol.

The crude mixture of 897 grams of perillyl acetate, perillyl alcohol, and by-products was placed in a three liter round bottom flask equipped with an overhead mechanical stirrer. To this mixture was added one liter of acetic anhydride and 50 ml. of pyridine. The resulting solution was stirred at room temperature for 10 hours. Vacuum distillation (80° C. at 0.7 mm Hg) provided 714 grams of pure perillyl acetate.

The following NMR Data were obtained on purified samples of Perillyl Acetate (B).

$^1$H NMR of perillyl acetate (B): ($CDCl_3$) δ 1.60–2.30 (m, 10H), 1.70 (s, 3H), 2.05 (s, 3H), 4.42 (br. s, 2H), 4.68 (br. s, 2H), 5.73 (br. s, 1H).

$^{13}$C NMR of perillyl acetate (B): (62.9 MHz $CDCl_3$) 153.9 (s), 133.8 (s), 120.3 (d), 107.6 (t), 65.0 (t), 36.8 (d), 31.2 (t), 30.4 (t), 28.1 (q), 23.4 (q) ppm.

EXAMPLE FOUR

The Saponification of Perillyl Acetate (B) to Perillyl Alcohol (A)

The alkaline hydrolysis of perillyl acetate to perillyl alcohol is a well established process, that follows. The 714 grams of perillyl acetate described above was diluted with three liters of ACS reagent grade methanol, followed by the addition of 500 grams of anhydrous sodium carbonate powder after which the mixture was stirred at room temperature for a ten hour period. The sodium salts were filtered off via suction filtration and washed with one liter of methanol. After removal of the methanolic solution under water aspirator, the resulting residue was extracted with tert butyl methyl ester (four liters). The combined etheral phases were dried over anhydrous magnesium sulfate, filtered and concentrated to a residue. This residue was vacuum distilled at 0.7 mm Hg (80–85° C.) to provide 530 grams of perillyl alcohol or a yield of 53% based on the starting beta pinene oxide.

The following NMR Data were obtained on purified samples of Perillyl Alcohol (A).

$^1$H NMR of perillyl alcohol (A): (250 MHz) δ 1.4–1.5 (m, 1H), 1.72 (s, 3H), 1.75–2.20 (m, 7H), 4.01 (br. s, 2H), 4.71 (br. s, 2H), 5.65 (br. s, 1H).

$^{13}$C NMR of perillyl alcohol (A): (62.9 MHz) (CDCl$_3$) 149.7 (s), 137.3 (s), 122.3 (d), 108.6 (t), 67.1 (t) 41.0 (d), 30.3 (t), 26.2 (t), 26.2 (t), 22.0 (t), 20.0 (q) ppm.

The quality of beta pinene oxide is important to the reaction. When freshly distilled epoxide is used the overall yield is about 50% on a 200 gram reaction. However the crude beta pinene oxide prepared from Rosemarel, as described earlier, afforded overall yields of 45–55%. Because beta pinene oxide is heat sensitive, its purification resulted in a limited loss of the material.

Anhydrous sodium carbonate powder is employed in the thermolysis as a scavenger for the generated acetic acid to prevent either double bond isomerization or acetylation. Because it is consumed during the pyrolysis, fresh sodium carbonate must be used in the hydrolysis. When ethanol is used the reaction is slow.

It was observed that the use of potassium carbonate in place of sodium hydroxide achieved complete deprotection of the acetate moiety but required twice as long reaction times whereas the use of the more economical base sodium hydroxide proceeded in a yield of less than 75% and produced p-cumene that was easily removed by distillation. Instead of a standard ethereal workup the product could also be isolated using steam distillation. However the low volatility of perillyl alcohol required long distillation times. Attempts to use less than a stoichiometric amount of base failed to promote complete removal of the acetate. Heating the methanolic solution to reflux served little in that the saponification was complete within an hour even at room temperature.

EXAMPLE FIVE

The Production of p-Menthene-7,8-Diol (D)

The initial step in the applicants second preferred method of producing perillyl alcohol and its acetate from beta pinene oxide is to react beta pinene oxide with water in the presence of an acid catalyst to form p-menthene-7,8-diol (D) as follows.

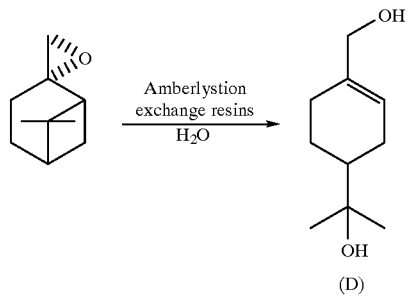

A five liter reactor, equipped with a sintered glass-frit and a stopcock at the bottom was charged with one kilogram of beta pinene oxide, one liter of distilled water, and twenty grams of Amberlyst 15 ion exchange resin beads. The mixture was stirred at room temperature. After approximately thirty minutes, the internal temperature of the reaction mixture increased to roughly 70° C. TLC analysis indicated that all the epoxide had been converted into diol. The reaction mixture was cooled to 0° C. after which one liter of reagent grade acetone was added. The reaction mixture was stirred for fifteen minutes and the resulting mixture was drained from the reactor. The reactor and beads were washed with an additional 500 ml of reagent grade acetone. The combined acetone phases could be concentrated directly on a rotary evaporator but greater than six hours was required. The crude diol obtained was then placed on a vacuum pump at 1–1.5 mm Hg and then heated to 50° C. to remove residual water. A one kilogram scale reaction using beta pinene oxide and this workup procedure gave virtually a quantitative yield of 1115 grams of crude diol D. TLC and NMR analysis indicated that less than five percent perillyl alcohol was produced in the formation of p-menthene-7,8-diol. No attempts were made to isolate the compounds.

Acetone could be removed from the combined organic phases by means of atmospheric distillation. One liter of toluene was then added to the reaction mixture to remove the remaining water through azeotrophic (atmospheric) distillation. The resulting mixture was then concentrated by means of distillation. The residue obtained did not require additional drying. A one kilogram scale reaction using beta pinene and this workup procedure gave 1121 grams of crude diol (D) or a 101% yield. The greater than quantitative yield was obtained because of the residual toluene.

When impure Rosemarel was used in the reaction mixture it was diluted with an inert hydrocarbon solvent, either petroleum ether or hexanes, in order to remove trace unreacted epoxide or contaminants in the starting material. For example when two kilograms of Rosemarel were used in this reaction, one liter of petroleum ether was added to the reactor. Upon completion of the reaction of Rosemarel and Amberlyst ion exchange resin, the resulting mixture was stirred for fifteen minutes and on standing three layers were observed: the top layer consisted of hydrocarbon solvent containing unreacted B-pinene, the middle layer consisted of water containing significant amounts of diol, and the bottom layer was a mixture of mostly diol and some water. The bottom two phases were drained from the reactor, combined and then concentrated. Evaporation of the hydrocarbon phase afforded recovered B-pinene. It is important to note that despite the use of an acid catalyst, the isomerization of beta pinene to alpha pinene did not occur.

Likewise water could be removed from the crude diol by lyophilization (freeze-drying). Crude diol (D) obtained in this fashion was not subjected to further vacuum-promoted drying.

No attempts were made to minimize either the amount of water necessary to carry out this reaction or the quality of acidic beads required to catalyze the reaction. It is very important that the acidic resin be removed before diol (D) is concentrated, by removing water azeotropicly or by using a rotary evaporator, because other means of dehydration give a low yield of perillyl alcohol and its isomer (H) along with several other byproducts as summarized in the scheme below.

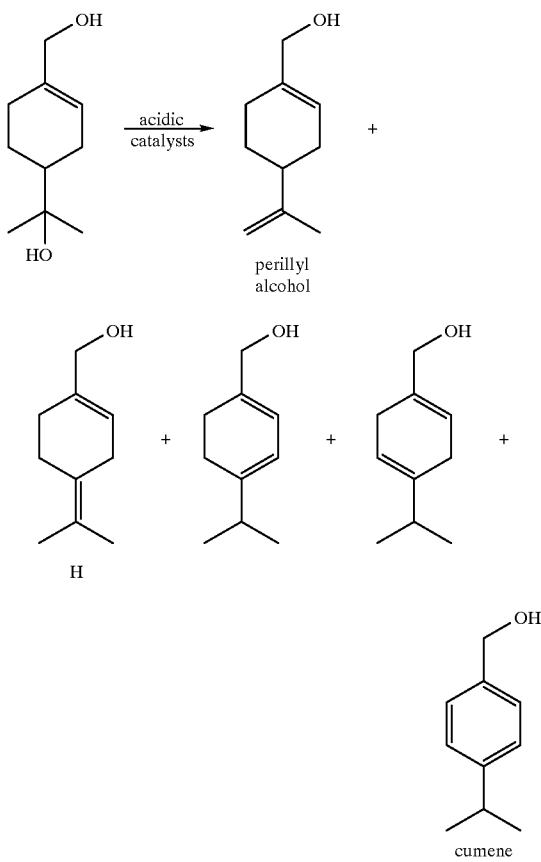

Longer exposure to acidic beads favored the production of these byproducts. It was not necessary to remove the beads when water was removed by freeze-drying (lyophilization). The use of a 10 mole percent of Amberlyst acidic resins generally permitted the reaction to be complete within a two-hour period. The use of small quantities of catalyst or milder acidic resins required longer reaction times (typically twelve hours) as did use of recycled beads. The use of an ice-bath allowed the reaction to be carried out without significant increases in the internal temperature. However, such cooling caused the reaction to be sluggish. In such cases the reaction was allowed to stir overnight at room temperature.

Although acetone was employed to insure a homogenous solution and was our preferred solvent, ethanol, methanol, and tetrahydrofuran were also successfully employed on 100-gram scale batches.

The diol (D) could be purified via distillation at 155–160° C. at 4 mm Hg. However, distillation was not necessary and the diol crystallized upon storage at 0° C. The following NMR data were obtained on a sample of the diol (D).

$^1$H NMR of diol D: (250 MHz) δ 1.16 (s, 3H), 1.17 (s, 3H), 1.20–2.40 (m, 7H), 3.96 (s, 2H), 5.64 (br.s, 1H).

$^{13}$C NMR of diol D: (250 MHz) 137.3 (s), 122.2 (d), 72.5 (s), 66.8 (t), 44.9 (d), 27.2 (t), 26.4 (q), 26.2 (t), 23.5 (t) ppm.

EXAMPLE SIX

The Preparation of p-Menth-1-en-7-Acetoxy-8-ol (E)

The applicants method of preparing p-menth-1-en-7-acetoxy-8-ol (E) is outlined below.

A two liter reactor was charged with 1115 grams of crude diol (D), six hundred (600) ml of reagent grade acetic anhydride and five (5) ml pyridine (catalytic quantity). The resulting mixture was stirred at room temperature for 1–8 hours until the TLC analysis indicated the reaction was completed. Within an hour of mixing the reagents together the internal temperature of the reaction rose to 75° C. Although TLC analysis indicated the reaction was virtually complete, the reaction was stirred overnight (for an additional eight hours) at room temperature as a precautionary measure. The reaction vessel was then equipped with an 18-inch vigreaux column and a fractional distillation apparatus and placed under vacuum at 1.5–2 mm Hg. Fractional distillation of the reaction mixture permitted the selective removal of unreacted acetic anhydride and the acetic acid formed in the course of the acetylation. The small amount of pyridine that was added to promote the reaction co-distilled with the acetic acid and acetic anhydride. TLC and NMR analysis indicated the 1465 grams of pot residue consisted of greater than 90% of the desired monoacetate (E), less than 5% perillyl acetate (B) and less than 5% diacetate (F). Although p-menth-1-en-7-acetoxy-8-ol (E) could be purified via fractional distillation at a BP of 135–140° C. and 1.5 mm Hg, no attempts were made to purify this mixture. The following NMR data were obtained on a distilled sample of monoacetate (E):

$^1$H NMR of monoacetate E: (250 MHz) δ 1.04 (s, 3H), 1.08 (s, 3H), 1.10–2.10 (m, 11H) 2.05 (s, 3H), 4.41 (br. s, 2H), 5.70 (br. s. 1H).

$^{13}$C NMR of monoacetate E: (250 MHz) 171.0, 132.6, 125.8, 72.5, 68.3, 44.6, 27.1, 26.7, 26.1, 23.3, 20.8 ppm.

It was observed that the selective acetylation worked best when a dry, concentrated solution of the diol (D) was used. On one occasion, acetylation was carried out on a one-kilogram scale using a toluene solution of the dissolved diol, produced by the azeotropic removal of water. The use of toluene as a solvent caused the acetylation to require heating at less than 50° C. for less than eight hours. The toluene had to be removed prior to conducting the next synthetic transformation. Since this reaction was exothermic, large reaction batches were cooled in an ice-bath that maintained the temperature below 50° C. without difficulty.

EXAMPLE SEVEN

The Preparation of Perillyl Acetate (B), and 7-acetoxy-p-menth-1,4(8)-diene (G)

To produce the antineoplastic agent perillyl acetate (B) from p-menth-1-en-7-acetoxy-8-ol (G), the applicants have used five different methods (a–e) to dehydrate p-menth-1- en-7-acetoxy-8-ol of which pyrolysis (a) is the preferred method. Each of these preparative procedures give useful mixtures of perillyl acetate (B) and its isomer, 7-acetoxy-p-menth-1,4(8)-diene. We have found these isomers can be easily separated in the final step only by using fractional distillation and an efficient vigreaux column. The dehydrations of diol (E) are depicted below.

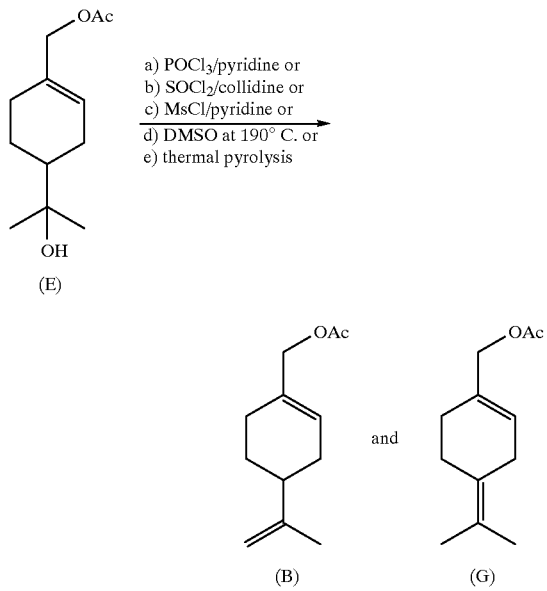

(a) The dehydration of (E) using phosphoryl chloride and pyridine

The dehydration of alcohols with phosphoryl chloride (also called phosphorous oxychloride) and pyridine is well established[12]. The dehydration of alcohol (E) gave both perillyl acetate (B) and its isomer (G) in varying yields.

A solution of 10.0 grams (47.moles) of alcohol (E) in 50 ml of dry pyridine was cooled to 0° C. and treated dropwise with 13 ml of phosphorous oxychloride and was allowed to stand at room temperature for twenty-four hours. The reddish-brown mixture decomposed by the cautious addition of water. The solution was extracted with ether, after which the ethereal solution was washed with 10% hydrochloric acid, water, and brine and dried over anhydrous magnesium sulfate. The solvent was evaporated and the oily residue was fractionally distilled to afford 5.48 grams (60%) of an inseparable 1:1 mixture of acetates (B) and (G) with a BP of 115–125° C. at 1.5 mm Hg having the following spectral data:

$^1$H NMR of a 1:1 mixture of acetates (B) and (G): (250 MHz) δ 1.40–1.50 (m, 0.5H), 1.47 (s, 0.75H), 1.52 (s, 0.75H), 1.71 (s, 1.5H), 2.04 (s, 3H), 1.75–2.20 (m, 5H), 2.30 (t, 0.5H) 2.82 (br. s, 0.5H), 4.43 (br. s, 2H), 4.69 (br. s, 2H), 5.72 (br. s, 1H).

While it was easy to carry out the procedure, the need to use phosphorous oxychloride and pyridine limits its commercial appeal. Moreover, the ratio of acetate to isomers varied from 1:1 to 5:1 as a function of the scale of the reaction, with less favorable ratios observed on the larger scale reactions with a dehydration yield that varied from 50–60%.

(b) The dehydration of (E) using thionyl chloride and 2,4,6-collidine

Thionyl chloride in pyridine is a more powerful reagent system for the dehydration of alcohols than phosphoryl chloride in pyridine[13]. In the preceding experiment we observed a 1:1 to 5:1 ratio of dehydration isomers using pyridine as the base. 2,4,6-collidine (also called 2,4,6-trimethylpyridine) is a more hindered base than pyridine and was examined with thionyl chloride for its ability to dehydrate (E) in hopes of producing a more favorable ratio of acetate to isomers.

A solution of 2.43 grams (11.4 mmol) of alcohol (E) in 25 ml of 2,4,6-collidine was cooled to −40° C. and treated dropwise with 1.7 ml of thionyl chloride (23.3 mmol). The reaction was essentially complete within five minutes. The reaction was quenched with saturated aqueous copper sulfate (5 ml) and was extracted with ether (3×100 ml). The combined ethereal extracts were washed with 10% hydrochloric acid, brine, and then dried over anhydrous magnesium sulfate. The solvent was evaporated and the oily residue was distilled to afford 1.76 grams of acetates (B) and (G) in a 80% yield. It was observed that the ratio of acetate to isomers varied from 5:1 on a 10-gram scale reaction to 10:1 on a one-gram reaction. The dehydration yield varied between 70–80%. Pyridine or DBU [1,8-diazabicyclo (5.4.O) undec-7-ene] was also used in this reaction with a less favorable yield of 2.5:1 of B:G.

(c) The dehydration of (E) using methanesulfonyl chloride and pyridine

The combination of methanesulfonyl chloride and pyridine is a powerful method of dehydrating alcohols. When this combination was used to dehydrate (E), the reaction gave both perillyl acetate and its isomers in a disappointing ratio.

A solution of 1.0 gram (4.71 mmol) of alcohol (E) was treated dropwise with 0.4 ml of methanesulfonyl chloride (5.2 mmol) and 0.8 ml of dry pyridine (9.9 mmol) at room temperature. The reaction was complete within three hours. The reaction was diluted with 200 ml. of ether and the ethereal phase was washed with brine and dried over anhydrous magnesium sulfate. The solvent was evaporated and the oily residue was distilled to afford 840 milligrams of acetates (B) and (G) in a yield of 92%. The ratio of the acetate to isomers was consistently 2.5:1 regardless of the reaction scale. Despite the rapidity of this dehydration and its ease of operation, this procedure could not be modified to improve the selectivity of isomer formation.

(d) The dehydration of (E) using dimethyl sulfoxide

Heated solutions of dimethyl sulfoxide (DMSO) can dehydrate secondary or tertiary alcohols. Heating 65 grams of alcohol (E) (0.30 moles) in 65 ml of DMSO at 190° C. for ninety minutes resulted in the rapid formation of acetates (B) and (G). The reaction mixture was cooled to 0° C. and then poured into an equal volume of water. The resulting mixture was then extracted with three 200 ml portions of tert-butyl methyl ether. The combined ethereal extracts were washed with brine, dried over anhydrous magnesium sulfate, filtered and concentrated to afford 52 grams of a crude oil. NMR analysis indicated this oil to consist of a 5:1 mixture of (B) to (G) respectively. Although the dehydration yield was consistently greater than 85%, hot DMSO generated various foul smelling vapors that could not be identified nor prevented. The addition of inorganic bases such as barium or calcium oxide suppressed the decomposition of dimethyl sulfoxide but also retarded the rate of dehydration. This reaction is amenable to a large scale process that is in quantities greater than 250 grams.

(e) The pyrolysis of (E)

As described earlier the thermal elimination of alcohols by either passing the substrate through a hot tube or by dropping the substrate onto a hot surface while under vacuum is capable of producing olefins. The applicants have found that the flame distillation of alcohol (E) gives virtually a quantitative yield of the acetates (B) and (G) in roughly a 6:1 ratio respectively as follows.

A two liter reactor was charged with 1200 grams of alcohol (E), equipped with a magnetic bar, and efficient 24-inch silver-jacketed vigreaux column, a fractional distillation apparatus equipped with a thermometer (to measure the internal temperature), was placed under vacuum of 1.5 mm Hg. A hand-held Bunsen burner was used to heat the reaction and govern the rate of distillation. The flame-heated distillation flask never recorded an internal temperature greater than 135° C. Thus the pyrolysis undoubtedly occurred on the sides of the distillation flask. The rate of the distillation was controlled by hand such that only the olefin and any water generated on pyrolysis were distilled over. Overheating of the distillation vessel resulted in the distillation of only alcohol (E). In this manner any dehydration product produced due to a hand-held Bunsen burner pyrolysis was allowed to distill over preferentially. In a fourteen-hour period over 1050 grams of the pyrolyzed material was collected and consisted of perillyl acetate, its isomer (G) and water that was produced through the dehydration. The pot residue consisted of viscous polymerized material that was formed due to overheating. The applicants established that the pyrolytic dehydration of alcohol (E) requires temperatures greater than 700° C. and less than 1875° C. that is the temperature of an air-operated natural gas Bunsen burner. Trace dehydration products were obtained using a Pope Wiped Film molecular still[17]. No dehydration products were obtained by slowly dropping alcohol (E) onto the surface heated at 400° C. under vacuum and capturing the pyrolysate. Both processes served only as alternative means of purifying (distilling) alcohol (E).

(f) Flash Vacuum Thermolysis (Pyrolysis) of (E)

Flash vacuum thermolysis (FVT) utilizes an unfilled quartz tube heated under low pressure and to a specified temperature that prevents tar formation and generally gives a high mass recovery. A large-scale FVT of acetate (G) as is outlined below:

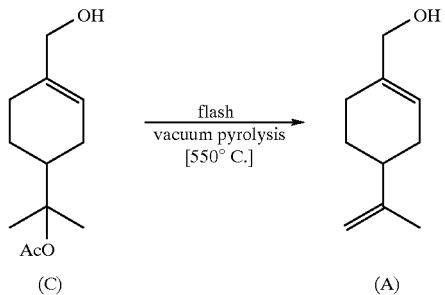

FIG. 1 depicts the reaction set-up used to carry out this flash vacuum pyrolysis. Because of the large volume of substrate to be pyrolyzed, an equal-pressure addition funnel is needed to prevent introduction of air into the pyrolysis system in that air causes problems once the pyrolysis begins. A 20 mm OD quartz tube, equipped with vigreaux-like indentions to increase the surface area of the quartz vessel, was heated to 600° C. in a Lindberg heavy-duty furnace. Two external traps maintained at −78° C. were employed. The second trap was a precautionary measure employed to maintain the proper operation of the vacuum pump. Perillyl alcohol was prepared as follows:

A five-Liter reactor, equipped with an efficient water-cooled condenser, a thermometer and a mechanical stirrer, was charged with 1000 grams of beta pinene oxide. The reaction vessel was cooled to 0° C. using an ice bath. Glacial acetic acid (540 ml) was then added in a single portion. Within minutes the internal temperature of the reaction mixture increased to roughly 150° C. TLC analysis indicated that all the epoxide was converted into either perillyl alcohol directly in an estimated yield of greater than 40% or acetate G in a yield of greater than 40% or an undetermined amount of diacetate (based on integration of NMR spectra). This 1600 grams of material was used directly in the next reaction without further characterization or purification. Of the 1600 grams of crude reaction mixture obtained, one-half was placed into the one-liter distillation flask and the other half was placed into the liter-dropping funnel. The reaction apparatus was placed under vacuum at 1.5 mm Hg and the distillation flask was then heated to 110° C. and then gradually increased to 150° C. Under these conditions the acetic acid present in the crude mixture was removed first and collected in the traps. Alternatively before hand, the crude reaction mixture was fractionally distilled under vacuum so that all the volatiles that had a boiling point less than 85° C. were removed. The resulting residue was then placed into the distillation pot shown in FIG. 1. Once all the volatiles were removed in a twelve hour period, passage of the vapors of acetate (B) at 150° C. and 1.5 mm Hg through the hot quartz tube at 600° C. resulted in the elimination of acetic acid and formation of acetates (B) and (G). A low evaporation rate of 20 grams per hour was used. After thirty-six hours, 1600 ml of distillate was collected. TLC and NMR analysis indicated the distillate consisted of acetic acid, perillyl alcohol and a small amount of perillyl acetate. The high temperatures cause the loss of the C(7) acetate to directly afford perillyl alcohol. The combined distillate was distilled using an efficient five-foot silver jacketed vigreaux column to provide 700 ml of acetic acid, 405 grams of perillyl alcohol in a yield of 36%, 58 grams of alcohol (H) in a yield of 5% and more than 400 grams of an unknown polymer. It was observed that rapid evaporation rates lead to incomplete pyrolysis and the isolation of unreacted (G) in the distillate. More importantly, heating (G) at temperatures greater than 50° C. above its boiling point (to achieve a higher evaporation rate) lead to the formation of a thick viscous oil that did not undergo pyrolysis and hence decreased the efficiency of the overall transformation. In general, a tube furnace oven temperature greater than 500° C. but less than 700° C. was adequate. Analytical runs in 10-gram scales indicated the optimum temperatures were between 550° C. and 600° C. Slow distillation rates allowed the conversion to occur in one pass. However, pyrolyzed material which contained unreacted acetate (E) was resubmitted for a second pyrolysis without decomposition of the perillyl alcohol previously produced.

It is recognized by the applicants that a modification of the pyrolysis equipment and the conditions of the pyrolysis can increase or decrease the yield of perillyl alcohol.

EXAMPLE EIGHT

Saponification of Perillyl Acetate (B) and Its Isomer (G) to Perillyl Alcohol

To a two-liter reactor charged with 1050 grams of a mixture of perillyl acetate (B), its isomer (G), and an undetermined amount of water, was added two liters of reagent grade menthol. One kilo of sodium carbonate was added and the reaction mixture was stirred for two hours at room temperature. The methanol was removed using a rotary evaporator to provide a residue that was extracted with tert-butyl methyl ether (3×200 ml). The combined ethereal extracts were dried over anhydrous magnesium sulfate, filtered, and concentrated to give 997 grams of a crude mixture of perillyl alcohol and alcohol (H). The resulting oily residue was distilled under vacuum at 1.5–2.0 mm Hg using an efficient five-foot silver jacketed vigreaux column. The fraction collected between 115° C. to 125° C. at 1.5 mm Hg represented 695 grams of perillyl alcohol with a yield of 85%.

Continued distillation (125–135° C. at 1.5 mm Hg) provided 102 grams of the tetrasubstituted olefin (H) having the following spectral data:

$^1$H NMR of alcohol (H): (250 MHz) δ 1.64 (s, 3H), 12.68 (s, 3H), 1.75–2.20 (m, 4H), 2.32 (t, 1H), 2.78 (br.s, 1H), 3.97 (br. s, 2H), 4.69 (br. s., 1H), 5.60–5.70 (m, 1H).

EXAMPLE NINE

Formulations that Incorporate Perillyl Alcohol to Kill Bacteria and Yeast

The following formulations are prepared using perillyl alcohol in liquids, gels, soaps, pastes, creams, ointments, suppositories, tampons, aerosols, and emulsions. When bacteria, or yeast are treated with perillyl alcohol containing formulations, the formulations kill or prevent the growth of bacteria and yeast.

| CHEMICAL | % OF TOTAL | RANGE | ACTION |
|---|---|---|---|
| A. LIQUIDS | | | |
| 1. SOLUTIONS OR SPRAYS | | | |
| a. Perillyl Alcohol | 5.0% | 0.1–50% | bactericide |
| Corn Oil | 95.0% | 50–99.9% | diluent |
| | 100.0% | | |
| b. Perillyl Alcohol | 1.0% | 0.1–50% | bactericide |
| Ethyl Alcohol | 99.0% | 50–99.9% | diluent |
| | 100.0% | | |
| 2. MOUTHWASH | | | |
| a. Perillyl Alcohol | 50.0% | 0.1–50% | anti-yeast |
| Flavor | 2.0% | 1–5% | flavor |
| Ethyl Alcohol | 48.0% | 45–98.9% | diluent |
| | 100.0% | | |
| B. DENTIFRICE | | | |
| 1. LIQUID | | | |
| Liquid soap concentrate | 5.0% | 2–10% | surfactant |
| Saccharin | 0.2% | 0.1–1.0% | flavor |
| Clove Oil | 1.0% | 0.5–3.0% | flavor |
| Cinnamon Oil | 0.5% | 0.5–3.0% | flavor |
| Peppermint Oil | 0.5% | 0.5–3.0% | flavor |
| Ethyl Alcohol | 42.6% | 29.5–95.3% | diluent |
| Color | 0.2% | 0.1–0.5% | color |
| Perillyl Alcohol | 50.0% | 1–50% | bactericide |
| | 100.0% | | |
| 2. GEL | | | |
| Sodium monofluorophosphate | 0.8% | 0.5–1.5% | anti-plaque |
| Perillyl Alcohol | 50.0% | 1–50% | bactericide |
| Hydrated silica xerogel | 10.0% | 8–15% | abrasive |
| Hydrated thickening silica | 8.5% | 5–10% | binder |
| Sorbitol 70% solution | 18.8% | 5–73.3% | humectant |
| Polyethylene glycol 32 | 5.0% | 3–7% | bodying agent |
| Sodium lauryl sulfate | 1.5% | 1–2% | surfactant |
| Carboxymethyl cellulose gum | 1.0% | 0.5–2% | binder |
| S D alcohol | 1.0% | 0.5–2% | stabilizer |
| Flavor | 3.0% | 2–4% | flavor |
| Saccharin | 0.2% | 0.1–0.5% | flavor |
| F D & C Green #3 | 0.1% | 0.1–0.5% | color |
| F D & C Yellow #1 | 0.1% | 0.1–0.5% | color |
| | 100.0% | | |
| 3. PASTE | | | |
| Sodium monofluorophosphate | 0.8% | 0.5–1.5% | anti-plaque |
| Perillyl Alcohol | 50.0% | 1–50% | bactericide |
| Dicalcium phosphate dihydrate | 22.0% | 20.4–30% | abrasive |
| Water | 16.0% | 11.1–69.5% | diluent |
| Glycerine | 5.1% | 4.5–12.5% | bodying agent |
| Flavor | 2.0% | 2–3% | flavor |
| Sodium lauryl sulfate | 1.5% | 1–2% | surfactant |
| Carboxymethyl cellulose gum | 1.4% | 0.5–2.0% | binder |
| Tetrasodium pyrophosphate | 1.0% | 0.5–2.0% | binder |
| Sodium saccharin | 0.2% | 0.1–0.5% | flavor |
| | 100.0% | | |
| C. OINTMENTS & SUPPOSITORIES WITH AND WITHOUT HYDROCORTISONE | | | |
| 1. OINTMENT WITH HYDROCORTISONE | | | |
| Perillyl Alcohol | 1.0% | 0.1–15.0% | bactericide |
| Polyethylene glycol 3350 | 59.5% | 48.5–59.7% | bodying agent & emulsifier |
| Polyethylene glycol 400 | 39.5% | 31.5–39.7% | bodying agent & emulsifier |
| Hydrocortisone | 1.0% | 0.5–5.0% | anti-inflamatory |
| | 100.0% | | |
| 2. OINTMENT WITHOUT HYDROCORTISONE | | | |
| Perillyl Alcohol | 1.0% | 0.1–15.0% | anti-yeast |
| Polyethylene glycol 3350 | 59.5 | 51.0–59.95% | bodying agent & emulsifier |
| Polyethylene glycol 400 | 39.5% | 34.0–39.95% | bodying agent & emulsifier |
| | 100.0% | | |
| 3. SUPPOSITORY WITHOUT HYDROCORTISONE | | | |
| Perillyl Alcohol | 1.0% | 0.1–15% | anti-yeast |
| Polyethylene | 9.5% | 51.0–59.95% | bodying |

| CHEMICAL | % OF TOTAL | RANGE | ACTION |
|---|---|---|---|
| glycol 1000 | | | agent & emulsifier |
| Polyethylene glycol 3350 | 39.5% | 34.0–39.95% | bodying agent & emulsifier |
| | 100.0% | | |

4. SUPPOSITORY WITH HYDROCORTISONE

| CHEMICAL | % OF TOTAL | RANGE | ACTION |
|---|---|---|---|
| Perillyl Alcohol | 1.0% | 0.1–15% | anti-yeast |
| Polyethylene glycol 1000 | 74.0% | 60.0–75.2% | bodying agent & emulsifier |
| Polyethylene glycol 3350 | 24.0% | 20.0–24.2% | bodying agent & emulsifier |
| Hydrocortisone | 1.0% | 0.5–5.0% | anti-inflammatory |
| | 100.0% | | |

D. CREAMS WITHOUT HYDROCORTISONE

| CHEMICAL | % OF TOTAL | RANGE | ACTION |
|---|---|---|---|
| Perillyl Alcohol | 1.0% | 0.1–15.0% | bactericide |
| Cetyl alcohol | 15.0% | 12.0–18.0% | thickener |
| Arlacel 165 ** | 5.0% | 3.5–7.5% | emulsifier |
| Sorbitol 70% solution | 5.0% | 3.5–8.0% | humectant |
| Water | 74.5% | 51.5–80.9% | diluent |
| | 100.0% | | |
| Perillyl Alcohol | 1.0% | 0.1–15.0% | anti-yeast |
| Spermaceti wax | 12.5% | 10.0–15.0% | thickener |
| Sorbitan monostearate | 10.0% | 7.5–12.5% | emulsifier |
| Polyethylene 20 Sorbitan monostearate | 6.0% | 4.0–8.0% | emulsifier |
| Water | 75.5% | 49.5–78.4% | diluent |
| | 100.0% | | |

E. CREAMS WITH HYDROCORTISONE

| CHEMICAL | % OF TOTAL | RANGE | ACTION |
|---|---|---|---|
| Perillyl Alcohol | 1.0% | 0.1–15.0% | anti-yeast |
| Cetyl alcohol | 15.0% | 12.0–18.0% | thickener |
| Arlacel 165 ** | 5.0% | 3.5–7.5% | emulsifier |
| Sorbitol 70% solution | 5.0% | 3.5–8.0% | humectant |
| Hydrocortisone | 1.0% | 0.5–5.0% | anti-inflammatory |
| Water | 73.0% | 46.5–80.4% | diluent |
| | 100.0% | | |

\* Croda, Inc., 51 Madison Ave., New York, New York 10010
\*\* Glycerol monostearate and polyoxyethylene stearate ICI of America (Formerly Atlas Chemical Industries), Wilmington, Delaware 19899

F. TAMPONS

| CHEMICAL | % OF TOTAL | RANGE | ACTION |
|---|---|---|---|
| Perillyl Alcohol (2 cc) 2 Gm | 8.0% | 1–15% | bactericide |
| Tampon 23 Gm | 92.0% | 85–99% | reservoir |
| | 100.0% | | for bactericide |

G. AEROSOLS WITHOUT HYDROCORTISONE

| CHEMICAL | % OF TOTAL | RANGE | ACTION |
|---|---|---|---|
| Perillyl Alcohol | 5.0% | 0.5–50% | bactericide |
| Ethyl alcohol | 95.0% | 50–99.5% | diluent |
| | 100.0% | | |

Pressurized nitrogen propellant at 100–125 psig

| CHEMICAL | % OF TOTAL | RANGE | ACTION |
|---|---|---|---|
| Perillyl Alcohol | 10.0% | 0.5–50.0% | anti-yeast |
| Soybean Oil | 90.0% | 50.0–99.5% | diluent |
| | 100.0% | | |

Pressurized nitrogen propellant at 100–125 psig

H. AEROSOL WITH HYDROCORTISONE

| CHEMICAL | % OF TOTAL | RANGE | ACTION |
|---|---|---|---|
| Perillyl Alcohol | 10.0% | 0.5–50% | bactericide |
| Soybean oil | 98.0% | 45–99.0% | diluent |
| Hydrocortisone | 1.0% | 0.5–5.0% | anti-inflammatory |
| | 100.0% | | |

Pressurized nitrogen propellant at 100–125 psig

I. OIL IN WATER EMULSION

| | CHEMICAL | % OF TOTAL | RANGE | ACTION |
|---|---|---|---|---|
| (1) | Perillyl Alcohol | 0.1% | 0.1–50% | anti-yeast |
| (2) | Corn oil | 10.0% | 10–15% | oil |
| (2) | Arlacel 40** | 2.0% | 1–3% | emulsifier |
| (2) | Tween 40 | 3.0% | 2–4% | emulsifier |
| (3) | Water | 84.9% | 28–86.9% | diluent |
| | | 100.0% | | |

Heat (2) to 70° C. Heat (3) to 72° C. Add (3) to (2) with continuous agitation. When (3) and (2) cool to 40° C., add (1) with continuous agitation until room temperature is reached.

J. OIL IN WATER EMULSION WITH SOAP (FUNGICIDAL SOAP)

| | CHEMICAL | % OF TOTAL | RANGE | ACTION |
|---|---|---|---|---|
| (1) | Perillyl Alcohol | 1.0% | 0.1–25% | fungicide |
| (2) | Corn oil | 30.0% | 20.0–40.0% | oil |
| (2) | Arlacel 40** | 2.0% | 1.0–3.0% | emulsifier |
| (2) | Tween 40 | 3.0% | 2.0–4.0% | emulsifier |
| (2) | Liquid soap concentrate | 3.5% | 2.5–5.0% | surfactant |
| (3) | Water | 60.5% | 23–74.4% | diluent |
| | | 100.0% | | |

Heat (2) to 70° C. Heat (3) to 72° C. Add (3) to (2) with continuous agitation. When (3) and (2) cool to 40° C., add (1) with continuous agitation until room temperature is reached.

K. WATER IN OIL EMULSION

| | CHEMICAL | % OF TOTAL | RANGE | ACTION |
|---|---|---|---|---|
| (1) | Perillyl Alcohol | 1.0% | 0.1–25% | anti-yeast |
| (2) | Arlacel 186** | 3.0% | 2.0–4.0% | emulsifier |
| (2) | Soybean oil | 15.0% | 10.0–25.0% | oil |
| (2) | Ceresin wax | 0.5% | 0.3–0.6% | thickener |
| (2) | Beeswax | 0.5% | 0.3–0.6% | thickener |
| (2) | Tween 80 | 0.5% | 0.3–0.6% | emulsifier |
| (3) | Water | 79.5% | 44.2–87.0% | diluent |
| | | 100.0% | | |

Heat (2) to 70° C. Heat (3) to 72° C. Add (3) to (2) with continuous agitation. When (3) and (2) cool to 40° C., add (1) with continuous agitation until room temperature is reached.

L. PAINT

1. ENAMEL

| CHEMICAL | % OF TOTAL | RANGE | ACTION |
|---|---|---|---|
| Perillyl alcohol | 1.00% | 1–10% | anti-yeast |
| Titanium dioxide | 14.91% | 12–16% | pigment |

-continued

| CHEMICAL | % OF TOTAL | RANGE | ACTION |
| --- | --- | --- | --- |
| Calcium carbonate | 29.83% | 25–35% | pigment |
| Silicate | 4.81% | 3–6% | pigment |
| Soya alkyd resin | 25.72% | 22–28% | pigment (binder) |
| Mineral spirits | 23.73% | 5–37% | solvent (thinner) |
|  | 100.00% |  |  |
| 2. LATEX |  |  |  |
| Perillyl alcohol | 1.0% | 1–10% | anti-yeast |
| Titanium dioxide | 10.76% | 8–12% | pigment |
| Silicate | 12.91% | 10–16% | pigment |
| Calcium carbonate | 20.91% | 15–25% | pigment |
| Vinyl acrylic resin solids | 12.22% | 10–16% | vehicle (binder) |
| Glycol | 8.30% | 6–10% | solvent (thinner) |
| Water | 34.00% | 12–50% | solvent |
|  | 100.00% |  | (thinner) |

While only certain preferred embodiments of this invention have been shown and described by way of illustration, many modifications will occur to those skilled in the art and it is, therefore, desired that it be understood that it is intended herein, to cover all such modifications that fall within the true spirit and scope of this invention.

What is claimed is:

1. A process for preparing perillyl alcohol which comprises reacting beta-pinene oxide with an acidic reactant to produce an alcoholic derivative of beta-pinene oxide and treating that derivative to recover therefrom perillyl alcohol.

2. A process of claim 1 wherein beta-pinene oxide is reacted with glacial acetic acid in the presence of anhydrous sodium acetate to produce p-menth-1-en-8-acetoxy-7-ol; pyrolyzing said p-menth-1-en-8-acetoxy-7-ol; and recovering perillyl alcohol.

3. A process of claim 1 wherein beta-pinene oxide is reacted with water in the presence of an acidic exchange resin catalyst to produce p-menthene-7,8-diol; reacting said diol with acetic anhydride in the presence of pyridine as a catalyst to produce 7-acetoxy-p-menth-1-en-8-ol; dehydrating said 7-acetoxy-p-menth-1-en-8-ol to produce perillyl acetate and saponifying said perillyl acetate to perillyl alcohol.

4. A process of claim 2 wherein a mixture of fused sodium acetate, glacial acetic acid and as a catalyst a strongly acidic macroreticular exchange resin was stirred and cooled to room temperature; beta-pinene oxide was added slowly to said mixture as the temperature of acid mixture was increased to about 65° C.; after said mixture had returned to room temperature glacial acetic acid was added thereto and the resulting mixture was filtered, washed with acetic acid, distilled, and washed to produce a product mixture of perillyl alcohol, p-menth-1-en-8-acetoxy-7-ol, and perillyl acetate; and pyrolyzing said product mixture to produce perillyl alcohol.

5. A process of claim 3 wherein beta-pinene oxide is reacted with water in the presence of a strongly acidic macroreticular exchange resin as a catalyst to produce p-menthene-7,8-diol; reacting said diol with acetic anhydride in the presence of pyridine as a catalyst to produce 7-acetoxy-p-menth-1-en-8-ol; dehydrating said 7-acetoxy-p-menth-1-en-8-ol to produce perillyl acetate; and hydrating said perillyl acetate to perillyl alcohol.

6. The process of claim 5 wherein said dehydrating was accomplished in the presence of phosphoryl chloride and pyridine as catalytic agents.

7. The process of claim 5 wherein said dehydrating was accomplished in the presence of thionly chloride and collidine as catalytic agents.

8. The process of claim 5 wherein said dehydrating was accomplished in the presence of methanesulfonyl chloride and pyridine as catalytic agents.

9. The process of claim 5 wherein said dehydrating was accomplished in the presence of dimethyl sulfoxide as a catalyst.

10. The process of claim 5 wherein said dehydrating was accomplished by thermal pyrolysis.

11. The process of claim 10 wherein said thermal pyrolysis was accomplished by means of a process of flash vacuum thermolysis at about 550° C.

* * * * *